United States Patent [19]

Grabitz et al.

[11] Patent Number: 4,677,073
[45] Date of Patent: Jun. 30, 1987

[54] PROCESS FOR PREPARING A STABILIZED SACCHAROMYCES CEREVISIAE CELL CULTURE

[75] Inventors: Ernst B. Grabitz, Casatenovo; Flavio Veneroni, Correzzana, both of Italy

[73] Assignee: Dox-al Italia S.p.A., Milan, Italy

[21] Appl. No.: 554,702

[22] Filed: Nov. 23, 1983

[30] Foreign Application Priority Data

Dec. 10, 1982 [IT] Italy .............................. 24673 A/82

[51] Int. Cl.$^4$ ............................................. C12N 1/18
[52] U.S. Cl. ...................................... 435/256; 424/93;
424/94; 426/60; 426/62; 435/260; 435/942

[58] Field of Search ..................... 424/93, 94, 95, 177,
424/359; 426/60, 62; 435/256, 260, 942, 800

[56] References Cited

U.S. PATENT DOCUMENTS

| | | | |
|---|---|---|---|
| 2,059,980 | 2/1935 | Bennett | 426/60 |
| 2,938,794 | 5/1960 | Herman | 435/260 |
| 3,041,249 | 6/1962 | Chen et al. | 426/62 |
| 3,542,648 | 11/1970 | Miller | 435/942 |

FOREIGN PATENT DOCUMENTS

| | | | |
|---|---|---|---|
| 8101415 | 5/1981 | PCT Int'l Appl. | 435/256 |
| 552953 | 4/1977 | U.S.S.R. | 435/256 |

*Primary Examiner*—Sam Rosen
*Assistant Examiner*—William J. Herald
*Attorney, Agent, or Firm*—Stevens, Davis, Miller & Mosher

[57] ABSTRACT

A process for preparing an integral *Saccharomyces cerevisiae* cell culture containing the cell bodies and all the products which form during the cell multiplication process, and for stabilizing the resultant product in order to maintain the cell integrity and biological activity unaltered for a long period.

The product obtained is useful in human and animal feeding as a growth factor and regulator of bacterial and enzymatic imbalance of the intestine, and as a protein additive in the cosmetics industry.

4 Claims, No Drawings

PROCESS FOR PREPARING A STABILIZED *SACCHAROMYCES CEREVISIAE* CELL CULTURE

This invention relates to a process for preparing an integral *Saccharomyces cerevisiae* cell culture containing the cell bodies and all the products which form during the cell multiplication process.

The product obtained is an aqueous suspension containing a very high concentration of *Saccharomyces cerevisiae* cells, which are stabilized by treatment with particular stabilizing agents during an operational stage which follows the multiplication stage.

The effect of the stabilization is to prevent or strongly retard ageing of the cells, and to maintain their integrity and biological activity intact for a long period, so preventing product degradation.

The product obtained contains a large quantity of enzymes, coenzymes, ferments, group B vitamins, nucleotides, nucleosides, free amino acids and RNA acid. Particularly useful products are obtained from *Saccharomyces cerevisiae* strains having high resistance in an acid environment (eg. gastric juices) and towards antibiotics. These product characteristics make it particularly suitable and effective as a human and animal food additive, as a growth factor and intestinal bacterial flora regulator. Its action is both prophylactic and curative in many affections in the human and veterinary field deriving from enzymatic and bacterial imbalance of the intestine.

The new product has also given surprising results in the cosmetics field as a highly active protein additive.

The cell multiplication process according to the present invention is carried out by adding the following ingredients to an aqueous suspension of fresh yeast constituted by selected strains of *Saccharomyces cerevisiae*:

sodium chloride in a quantity of 0.2-2.5% by weight of the total process activators, namely: mono and disaccharides (dextrose, lactose etc.) to the extent of 0.5-5% by weight of the total; inositol or magnesium sulphate to the extent of 0.04-0.1% lithium, calcium or magnesium chloride to the extent of 0.2-1.5%; calcium or magnesium nitrate, calcium salts of organic acids such as lactate, acetate, gluconate or pantothenate, sodium acetate, sodium pyruvate or glutathione, to the extent of 0.01-2%.

suspension stabilizers such as microgranular cellulose, carboxymethyl cellulose, gum arabic or other natural substances able to form colloids, hydrated silica or silicates.

The suspension is kept at a temperature of between 40° to 70° C. under agitation for a time of 0.5-5% hours.

The aforesaid cell culture is stabilized according to the present invention by adding one or more of the stabilizing additives listed hereinafter, and keeping the aqueous solution again under agitation at 45°-70° C. for a time of between 20 to 40 minutes.

The stabilizers comprise:

benzoic, sorbic, propionic, formic, acetic, tartaric, ascorbic or lactic acid, and lactic ferments ammonium formate phenols, hydroquinones and derivatives, benzyl alcohol and derivatives alkyl esters of p-hydroxybenzoic acid.

The quantity of stabilizer to be added varies over a wide range according to the substance or mixture of substances used. Some practical examples of the preparation and stabilization process according to the invention are given hereinafter by way of non-limiting illustration only.

The product, which is obtained in the form of a dense brown homogeneous liquid, can in all cases be used either as such or can be absorbed in hydrated silica. Alternatively, it can be dried in a fluidised bed in the presence of amorphous silica.

EXAMPLE 1

1000 kg of fresh yeast as starting material are fed into a 5000 liter enameled reactor, and the aqueous suspension is heated to 53° C. under agitation, after which the following additives are added: 25 kg of pure sodium chloride, 30 kg of dextrose and 5 kg of magnesium sulphate.

The mixture is kept under agitation for 60 minutes to obtain a homogeneous aqueous suspension, after which 2 kg of Nipagin (brand name of methyl or ethyl ester of p-hydroxybenzoic acid) are added.

Agitation is continued for a further 30 minutes to give a final product in the form of a homogeneous dense liquid, which can be used either as such or absorbed in hydrated silica, which is added in a quantity of 25 kg.

EXAMPLE 2

1000 kg of fresh yeast as starting material are fed into an enamelled 5000 liter reactor and the aqueous suspension heated to 45° C. under agitation, after which the following additives are added: 25 kg of sodium chloride, 20 kg of calcium gluconate, 2 kg of magnesium sulphate and 30 kg of lactose Farmacopea Ufficiale.

The mixture is kept under agitation for 4 hours 30 minutes to obtain a homogeneous aqueous suspension, after which 15 kg of microgranular cellulose and 2 kg of carboxymethyl cellulose are added.

The suspension is kept under agitation for a further 60 minutes, after which 30 kg of sorbic acid and 20 kg of ascorbic acid Farmacopea Ufficiale are added.

Agitation is continued for a further 30 minutes to obtain a final stabilized product which can be used either as such or dried in the presence of silica.

We claim:

1. A process for stabilizing a *Saccharomyces cerevisiae* cell culture, which comprises:
   (a) agitating an aqueous dispersion of fresh *Saccharomyces cerevisiae* and 0.02-2.5% by weight of sodium chloride; 0.5-5% by weight of mono- and disaccharides; 0.04-0.1% by weight of inositol; 0.04-0.1% by weight of magnesium sulfate; 0.2-1.5% by weight of lithium, calcium or magnesium chloride; and 0.01-2% by weight of one or more salts selected from the group consisting of calcium nitrate, magnesium nitrate, calcium lactate, calcium acetate, calcium gluconate, calcium pantothenate, sodium acetate, sodium pyruvate and sodium glutathionate; and a suspension stabilizer selected from the group consisting of microgranular cellulose, carboxymethyl cellulose, gum arabic, hydrated silica and silicates; at a temperature between 45° and 70° C. for 0.5-5% hours to form a homogenous suspension; and then
   (b) adding to said homogeneous suspension, while still being agitated at said temperature, a stabilizing agent selected from the group consisting of benzoic, sorbic, propionic, formic, acetic, tartaric, ascorbic and lactic acids; phenol, hydroquinone, benzyl alcohol; alkyl esters of p-hydroxybenzoic acid and ammonium formate.

2. A process as claimed in claim 1, wherein the stabilized homogeneous suspension obtained in step (b) is absorbed in hydrated silica.

3. A process as claimed in claim 1, wherein the stabilized homogeneous suspension obtained in step (b) is dried in a fluidized bed in the presence of amorphous silica.

4. A human or animal feed additive comprising a stabilized *Saccharomyces cerevisiae* cell culture prepared according to the process of claim 1.

* * * * *